(12) United States Patent
Sato

(10) Patent No.: US 10,856,814 B2
(45) Date of Patent: Dec. 8, 2020

(54) SUDDEN-ONSET SIGNAL PROCESSING DEVICE FOR BIOLOGICAL INFORMATION, AND SUDDEN-ONSET SIGNAL PROCESSING METHOD FOR BIOLOGICAL INFORMATION

(71) Applicants: KYUSHU INSTITUTE OF TECHNOLOGY, Kitakyushu (JP); AI TECHNOLOGY INC., Fukuoka (JP)

(72) Inventor: Yasushi Sato, Kitakyushu (JP)

(73) Assignees: KYUSHU INSTITUTE OF TECHNOLOGY, Kitakyushu (JP); AI TECHNOLOGY INC., Fukuoka (JP)

( * ) Notice: Subject to any disclaimer, the term of this patent is extended or adjusted under 35 U.S.C. 154(b) by 435 days.

(21) Appl. No.: 15/560,765

(22) PCT Filed: Mar. 22, 2016

(86) PCT No.: PCT/JP2016/058901
§ 371 (c)(1),
(2) Date: Sep. 22, 2017

(87) PCT Pub. No.: WO2016/152827
PCT Pub. Date: Sep. 29, 2016

(65) Prior Publication Data
US 2018/0078211 A1    Mar. 22, 2018

(30) Foreign Application Priority Data
Mar. 23, 2015   (JP) .................................. 2015-059287

(51) Int. Cl.
*A61B 5/00* (2006.01)
*A61B 5/0245* (2006.01)

(52) U.S. Cl.
CPC .......... *A61B 5/7214* (2013.01); *A61B 5/0245* (2013.01); *A61B 5/6893* (2013.01); *A61B 5/725* (2013.01)

(58) Field of Classification Search
USPC ..................................... 600/508–509; 607/17
See application file for complete search history.

(56) References Cited

U.S. PATENT DOCUMENTS

2004/0215262 A1* 10/2004 Ferek-Petric .......... A61N 1/368
                                                                607/17
2005/0043764 A1*  2/2005 Wesselink ............ A61N 1/3627
                                                                 607/9

(Continued)

FOREIGN PATENT DOCUMENTS

JP        S52-123582 A     10/1977
JP        2010-120493 A     6/2010

OTHER PUBLICATIONS

Jun. 14, 2016 International Search Report issued in International Patent Application No. PCT/JP2016/058901.

*Primary Examiner* — Nicole F Lavert
(74) *Attorney, Agent, or Firm* — Oliff PLC

(57) ABSTRACT

A device and method for detecting biological information without being affected by sudden-onset signal even when sudden-onset large vibration is caused while driving a vehicle or the like. Peak input and output values of a variable delay device are detected, and the difference between the values is determined by a subtractor. The difference is compared to a predetermined threshold to obtain a positive or negative output as an up/down selection output for an up/down counter. The output of the up/down counter is sent to a variable delay device with a clock generated based on an inputted peak signal of biological information to obtain a variable delay amount corresponding to one cycle of the biological information. When the subtractor output exceeds (Continued)

the predetermined threshold, a predetermined output voltage is generated, and an amplifier connected to the variable delay device is controlled so that the gain of the amplifier becomes zero.

4 Claims, 3 Drawing Sheets

(56) References Cited

U.S. PATENT DOCUMENTS

2007/0288183 A1* 12/2007 Bulkes ............... A61B 5/04012
          702/66
2008/0111653 A1* 5/2008 Lee ........................ H03K 5/131
          333/24 R \* cited by examiner

SUDDEN-ONSET SIGNAL PROCESSING DEVICE FOR BIOLOGICAL INFORMATION, AND SUDDEN-ONSET SIGNAL PROCESSING METHOD FOR BIOLOGICAL INFORMATION

TECHNICAL FIELD

The present invention relates to a sudden-onset signal processing device for biological information and a sudden-onset signal processing method for biological information, both for removing large vibration suddenly generated while detecting biological information such as heartbeat or the like.

BACKGROUND ART

In recent years, a method for acquiring biological information (such as heartbeat or the like) of a vehicle occupant during driving is proposed. In such a case, there is a concern that a sudden-onset abnormal signal might be mixed into a periodic signal (such as heartbeat or the like), depending on the road-surface condition and the like, and that will adversely affect the measurement of the biological information.

Patent Document 1 describes a biological information detecting device for detecting the biological information of a vehicle occupant using a radio wave-type unmodulated Doppler sensor.

In the technique described in Patent Document 1, a radio wave-type Doppler sensor is used to detect the movement of the vehicle occupant to thereby extract the biological information of the vehicle occupant, while calculating an estimated distance between the sensor and the vehicle occupant. Further, reliability of the biological information is determined based on the calculated estimated distance, and if the reliability is low, the biological information will be stopped from being outputted.

CITATION LIST

Patent Literature

Patent document 1: Japanese Unexamined Patent Application Publication No. 2010-120493

SUMMARY OF INVENTION

Technical Problem

However, when detecting the biological information of the vehicle occupant, there is a possibility that a sudden-onset large vibration might occur depending on road-surface condition and the like; in such a case, it is difficult to prevent malfunction caused by the sudden-onset noise with the technique described in Patent Document 1.

In view of the aforesaid problems, an object of the present invention is to provide a sudden-onset signal processing device and a sudden-onset signal processing method for biological information capable of suitably operating the detection function of the biological information without being affected by a sudden-onset signal even in a case where a sudden-onset large vibration is caused when driving a vehicle.

Solution to Problem

To solve the aforesaid problems and achieve the object of the present invention, a sudden-onset signal processing device for biological information according to an aspect of the present invention includes a variable delay device to which periodic biological information is inputted; a first peak detector that detects a peak value of an input signal of the variable delay device; and a second peak detector that detects a peak value of an output signal of the variable delay device. The sudden-onset signal processing device for biological information further includes a subtractor that performs subtraction between the output of the first peak detector and the output of the second peak detector; and a first comparator that compares the output of the subtractor with a first threshold, and that either outputs a positive output, if the output of the subtractor is larger than the first threshold, or outputs a negative output, if the output of the subtractor is smaller than the first threshold.

The sudden-onset signal processing device for biological information further includes a clock generator that generates a clock signal based on the output of the first peak detector; and an up/down counter that is either decremented (down counted), if the output of the first comparator is a positive output, or incremented (up counted), if the output of the first comparator is a negative output, and that supplies its output to the variable delay device with a clock from the clock generator.

The sudden-onset signal processing device for biological information further includes a second comparator (±comparator) that compares the output of the subtractor with a second threshold having a positive threshold value and a negative threshold value, and generates an output signal if the absolute value of the output of the subtractor exceeds the absolute value of the second threshold; and an amplifier that is connected to the variable delay device, and whose gain is controlled by the output of the second comparator.

A sudden-onset signal processing method for biological information according to an aspect of the present invention includes the steps of:
(a) detecting a peak of periodic biological information to be inputted to a variable delay device;
(b) detecting a peak of an output signal of the variable delay device;
(c) performing subtraction between a peak detection signal of the input of the variable delay device and a peak detection signal of the output of the variable delay device with a subtractor;
(d) comparing an output signal of the subtractor with a predetermined threshold with a comparator, and outputting either a positive output, if the output signal of the subtractor is larger than the threshold, or a negative output, if the output signal of the subtractor is smaller than the threshold, from the comparator;
(e) either decrementing (down counting) an up/down counter, if the output of the comparator is a positive output, or incrementing (up counting) the up/down counter, if the output of the comparator is a negative output;
(f) supplying the output of the up/down counter to the variable delay device with a clock generated based on the output of a peak signal of the biological information to be inputted to the variable delay device;
(g) generating a predetermined outputting voltage if the absolute value of the peak value of the output of the subtractor exceeds a predetermined second threshold; and
(h) supplying the outputting voltage to an amplifier connected to the output of the variable delay device, and controlling the amplifier so that the gain of the amplifier decreases only when the outputting voltage exists.

Advantageous Effects of Invention

With the sudden-onset signal processing device and the sudden-onset signal processing method for biological information, it is possible to properly detect the biological information without being affected by a sudden-onset signal, even in a case where a sudden-onset large vibration is caused when driving a vehicle.

DESCRIPTION OF EMBODIMENTS

Embodiments of a sudden-onset signal processing device for biological information according to the present invention will be described below with reference to the attached drawings.

Figure 1:
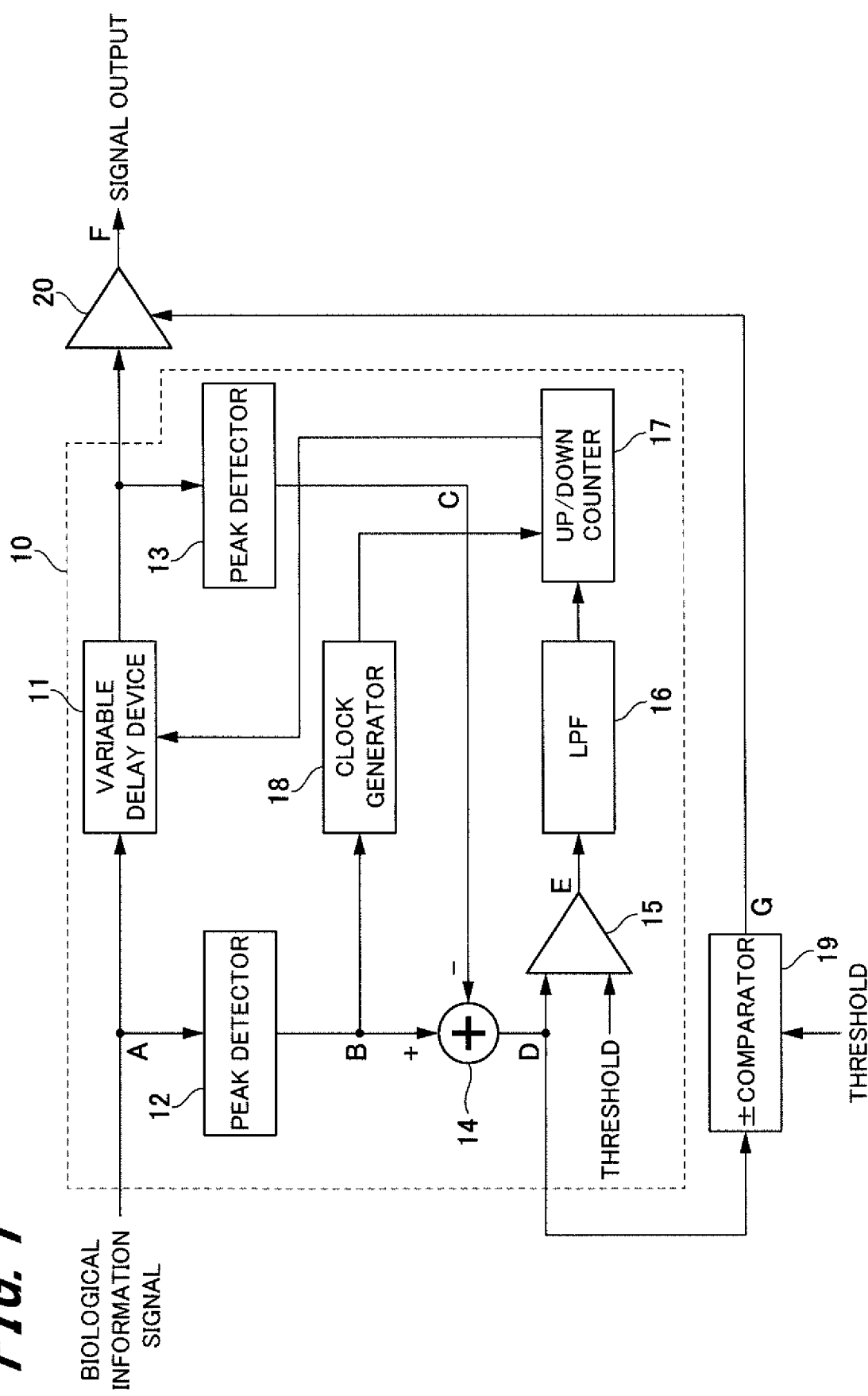
FIG. 1 is a block diagram showing a first embodiment of a sudden-onset signal processing device for biological information according to the present invention.

FIG. 1 is a block diagram for describing a first embodiment (hereinafter referred to as "present embodiment") of the sudden-onset signal processing device for biological information according to the present invention.

The sudden-onset signal processing device according to the present embodiment includes an adaptive delay device 10 to which a periodic biological information signal A (such as a heartbeat, a pulse wave or the like) is inputted. The adaptive delay device 10 used in the present embodiment is a portion surrounded by the broken line in FIG. 1. First, the configuration and operation of the adaptive delay device 10 will be described below.

<Configuration of the First Embodiment of the Present Invention>

The adaptive delay device 10 includes a variable delay device 11 to which the biological information signal A is inputted, a peak detector 12 (a first peak detector) to which the input of the variable delay device 11 is supplied, and a peak detector 13 (a second peak detector) to which the output of the variable delay device 11 is supplied.

The adaptive delay device 10 further includes a subtractor 14 (a first subtractor) that performs subtraction between the output of the peak detector 12 and the output of the peak detector 13, and a clock generator 18 that generates a clock based on the output of the peak detector 12.

The adaptive delay device 10 further includes a comparator 15 (a first comparator), an LPF (low-pass filter) 16 to which the output of the comparator 15 is supplied, and an up/down counter 17 to which the output of the LPF 16 is supplied; wherein the comparator 15 compares the output of the subtractor 14 with a predetermined threshold, and outputs voltage values with different polarities depending on whether the output of the subtractor 14 is larger or smaller than the threshold.

The aforesaid is the configuration of the adaptive delay device 10 used in the sudden-onset signal processing device for biological information of the present embodiment. The sudden-onset signal processing device for biological information further includes a ±comparator 19 (a second comparator) to which the output of the subtractor 14 is supplied. The sudden-onset signal processing device for biological information further includes an amplifier 20 which is connected to the output of the variable delay device 11, and to which the output of the comparator 19 is supplied.

<Operation of the First Embodiment of the Present Invention>

Next, the operation of the sudden-onset signal processing device for biological information of the present embodiment including the adaptive delay device 10 will be described below with reference to a waveform chart shown in FIG. 2.

The variable delay device 11 is a delay device whose delay amount can be set while following an input signal (a biological information signal) such as heartbeat, pulse wave or the like, so that its delay amount is set to one cycle of the input signal. Usually, the biological information signal A is a periodic signal, and therefore if there is no sudden-onset signal (such as disturbance), the input signal of the variable delay device 11 one cycle before and the output signal of the input signal of the variable delay device 11 one cycle after are substantially the same signal.

However, it is known that the cycle of the biological information (such as the heartbeat, pulse wave or the like) of human beings varies from person to person; and it is further known that the cycle of the biological information of human beings increases and decreases periodically even for the same person. In the sudden-onset signal processing device for biological information of the present embodiment, it is necessary to set the variable delay device 11 so that the delay amount of the variable delay device 11 is equal to the cycle of the biological information signal (such as the heartbeat or the like) of a person-to-be-measured.

Here, a case where the delay amount of the variable delay device 11 is smaller than one cycle of the biological information of the person-to-be-measured will be described below. In such a case, since a phase difference is caused between the output of the peak detector 12 and the output of the peak detector 13, the output of the subtractor 14 will not be "zero". In other words, in the case where the delay amount of the variable delay device 11 is smaller than one cycle of the biological information (i.e., in the case where the delay amount is not enough), if the output of the subtractor 14 is added to the comparator 15, the output of the comparator 15 will be a negative output. As a result, the output of the LPF 16 will be a selection signal for incrementing (up counting) the up/down counter 17.

On the other hand, in the case where the delay amount of the variable delay device 11 is larger than one cycle of the biological information, if the output of the subtractor 14 is added to the comparator 15, the output of the comparator 15 will be a positive output. As a result, the output of the LPF 16 will be a selection signal for decrementing (down counting) the up/down counter 17. The selection signal for increment or the selection signal for decrement is supplied from the LPF 16 to the up/down counter 17, and is supplied from the up/down counter 17 to the variable delay device 11 at timing of a clock from the clock generator 18.

As a result, the variable delay device 11 is controlled so that the delay amount of the variable delay device 11 is set to a delay amount equivalent to one cycle of the biological information signal A. That is, no matter what periodic biological information signal A is inputted, the variable delay circuit 11 will be set so that its delay amount becomes equal to the cycle of the periodic biological information signal A. In other words, a delay device whose cycle is equal to the cycle of the biological information (such as the heartbeat, the pulse wave or the like) is automatically set. Incidentally, the control of the delay amount of the variable delay device 11 described above is irrelevant to the value of the amplitude of the biological information signal A.

Next, a case where the delay amount of the variable delay device 11 is equal to the cycle of the biological information signal A and where a sudden-onset noise signal is mixed into the biological information signal A will be described below with reference to FIG. 2.

The biological information signal A is supplied to the peak detector 12, as well as supplied to the variable delay device 11 that delays the signal by one cycle. The output of the variable delay device 11 is supplied to the peak detector 13. The peak detectors 12, 13 are each a widely known peak hold circuit achieved by a program. The peak detectors 12, 13 each have a function of taking in a signal with the largest amplitude in the biological information signal A as a peak, and not detecting relatively small signal(s) included in the biological information signal A. For example, the heartbeat or the pulse wave includes a Q-wave with the largest amplitude, and other waves (such as a P-wave, a T-wave and the like) each with relatively small amplitude; by being passed through the peak detectors 12, 13, the effect of the other waves each with relatively small amplitude can be removed.

Figure 2:
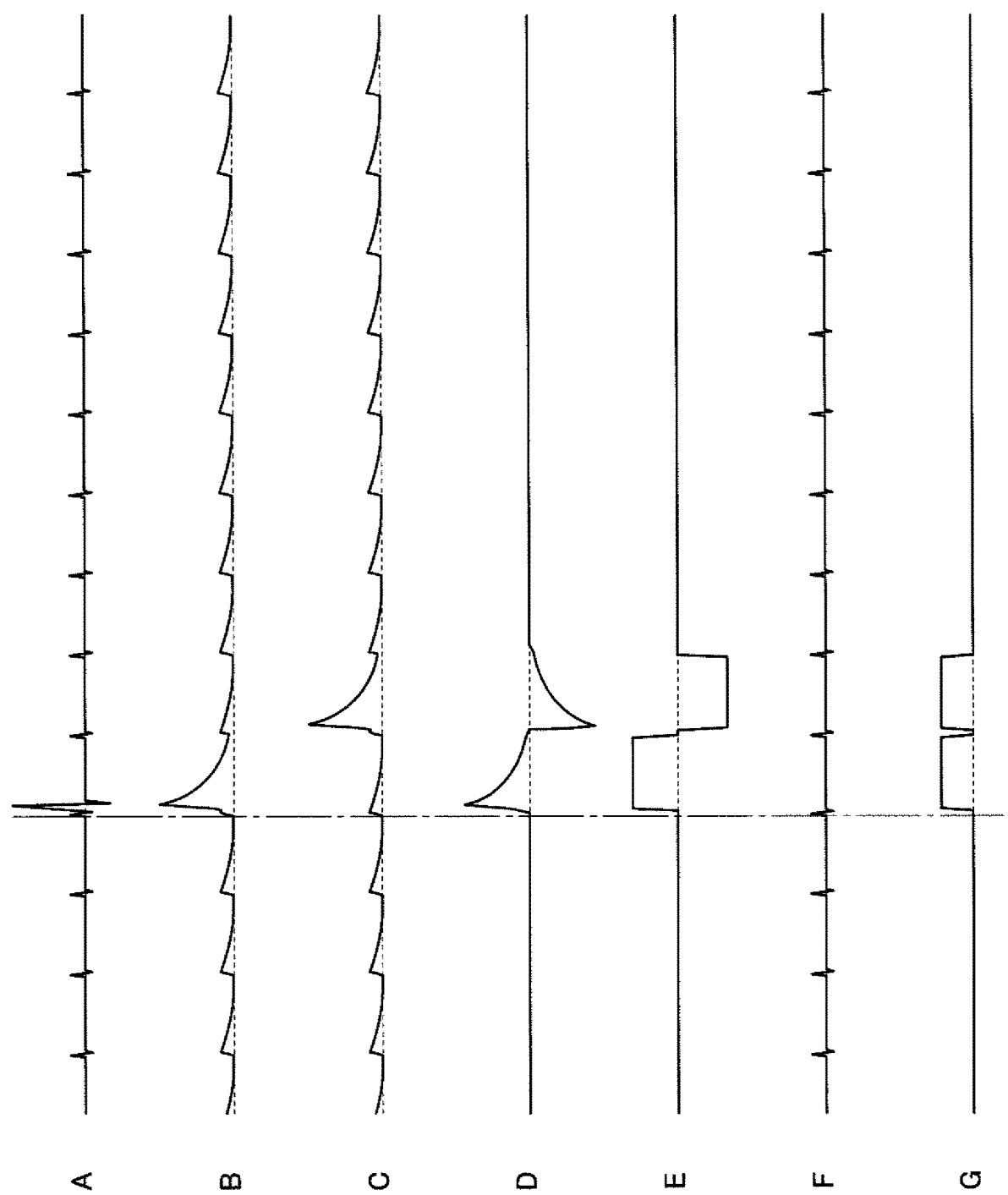
FIG. 2 is a waveform chart for explaining the operation of the first embodiment of the sudden-onset signal processing device for biological information according to the present invention.

As shown in FIG. 2, a signal B and a signal C are outputted respectively from the peak detector 12 and from the peak detector 13, wherein the signal B is a signal in which the peak of the biological information signal A is detected, and the signal C is a signal in which the peak of a signal obtained by delaying the biological information signal A by one cycle is detected. Here, as shown in FIG. 2, if sudden-onset noise is included in the biological information signal A, the output signal B of the peak detector 12 and the output signal C of the peak detector 13 are each outputted as a signal in which the portion including the noise has large amplitude.

Further, the outputs of the peak detector 12 and the peak detector 13 are supplied to the subtractor 14 where the output C of the peak detector 13 is subtracted from the output B of the peak detector 12. Here, if no sudden-onset noise signal is included in the biological information signal A, since the signal before being delayed by one cycle and the signal after being delayed by one cycle completely overlap each other, the output of the subtractor 14 will be "zero".

However, in the case where sudden-onset noise is included in the biological information, such as the biological information A shown in FIG. 2, since the noise is not a periodic signal, as shown in the waveform D of FIG. 2, the output of the subtractor 14 (which is obtained by subtracting the output of the peak detector 13 from the output of the peak detector 12) has a positive voltage and a negative voltage generated respectively in a noise portion before the biological information has been delayed by one cycle and a noise portion after the biological information has been delayed by one cycle.

The output signal D of the subtractor 14 is supplied to the comparator 15 where the signal D is compared to the predetermined threshold. The threshold set for the comparator is usually "0 V"; an output E of a square wave with a positive voltage and a negative voltage is obtained from the comparator 15, as shown the waveform E of FIG. 2. In the output E, the positive voltage functions as the selection signal for decrementing (down counting) the up/down counter 17, and the negative voltage functions as the selection signal for incrementing (up counting) the up/down counter 17. Thus, one selection signal for decrement (down count) and one selection signal for increment (up count) are added to the up/down counter 17, and therefore even if a noise signal is mixed into the biological information signal A, no change in delay amount of the variable delay device 11 will be caused by the noise signal.

The configuration and operation of the adaptive delay device 10, which is the essential part of the sudden-onset signal processing device for biological information of the present invention, have been described above.

In addition to the above description, the details about signal processing of the sudden-onset signal processing device of the present embodiment will be described below. The output of the subtractor 14 of the adaptive delay device 10 is supplied to the ±comparator 19 (the second comparator). The ±comparator 19 is a comparator which has two thresholds, one is positive, and the other one is negative. The thresholds are set to ±1V, for example. In other words, the ±comparator 19 outputs a square-wave pulse G as shown in FIG. 2 when the value of the output signal of the subtractor 14 (which is the input signal of the comparator 19) exceeds 1V, no matter such value is positive or negative.

The output signal G of the ±comparator 19 is supplied to the amplifier 20 connected to the output of the variable delay device 11, so that the gain of the amplifier 20 is controlled. For example, ON/OFF control for the gain of the amplifier 20 is performed by the output signal G. Thus, as shown in FIG. 2, the signal output F extracted as the output of the amplifier is a signal output whose noise components has been suppressed. In other words, it is possible to measure the biological information of the person-to-be-measured in a manner in which the noise included in the biological information signal A is moved, so that the measurement is not affected by a sudden-onset noise signal.

<Configuration and Operation of a Second Embodiment of the Present Invention>

Figure 3:
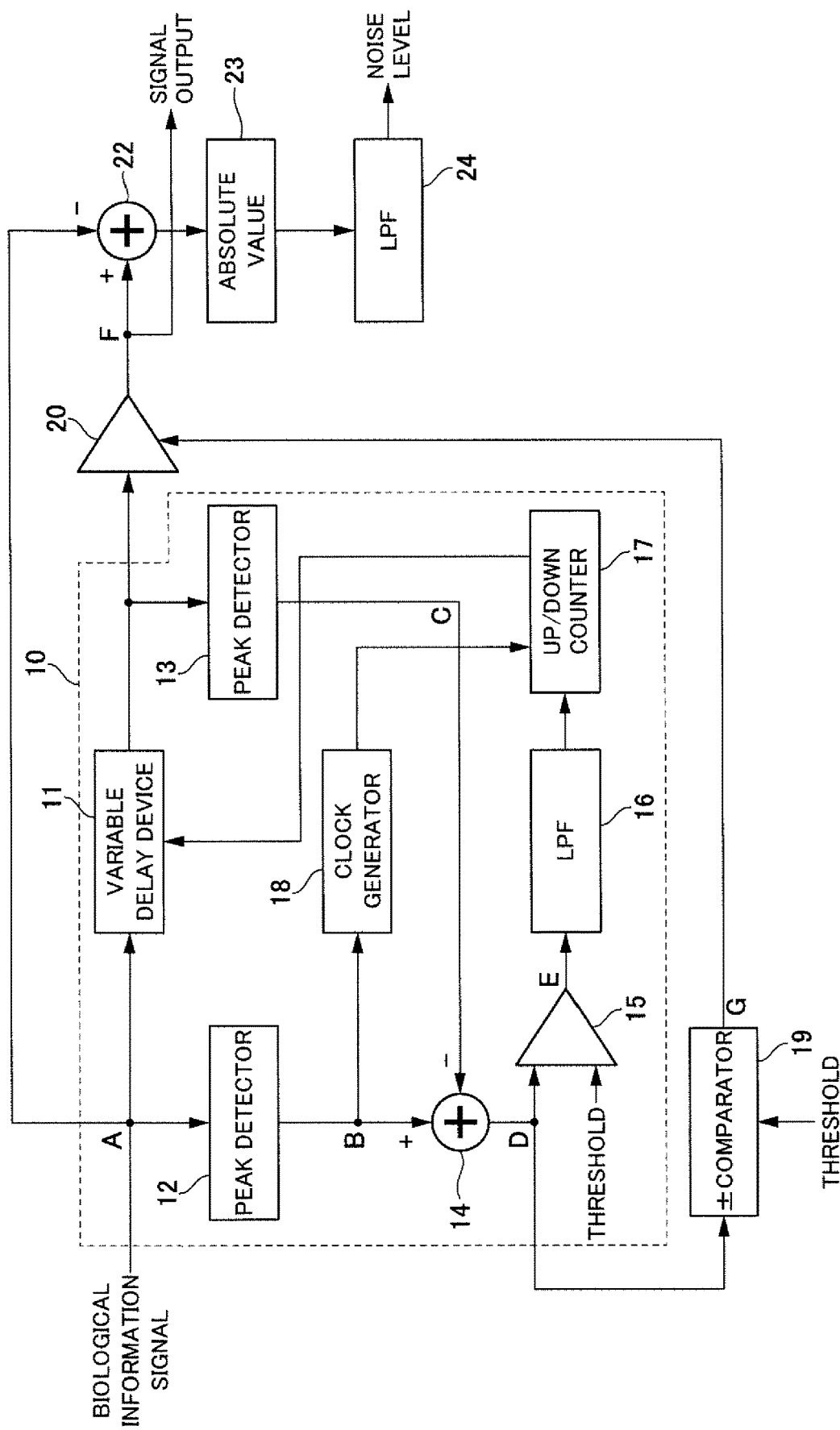
FIG. 3 is a block diagram showing a second embodiment of the sudden-onset signal processing device for biological information according to the present invention.

FIG. 3 is a block diagram showing a second embodiment of the sudden-onset signal processing device for biological information, the second embodiment being configured by changing a part of the sudden-onset signal processing device for biological information shown in FIG. 1. In FIG. 3, the configurations also described in FIG. 1 are denoted by the same reference numerals and the explanation thereof will not be repeated again.

The second embodiment shown in FIG. 3 differs from the first embodiment shown in FIG. 1 in that, in the second embodiment, a subtractor 22 (a second subtractor), an absolute value circuit 23 connected to the subtractor 22, and an LPF 24 are provided at the output of the amplifier 20.

The pure signal output F outputted from the amplifier 20 and obtained by removing the noise signal, and the biological information signal A including the noise signal are both supplied to the subtractor 22. Here, in the subtractor 22, the biological information signal A is subtracted from the signal output F, and therefore only the noise signal component is extracted from the subtractor 22. The noise signal component is supplied to the absolute value circuit 23; whether the noise signal component is positive or negative, a positive signal is supplied from the absolute value circuit 23 to the LPF 24. The LPF 24 smooths the output of the absolute value circuit 23, and outputs the smoothed signal as noise level.

With the second embodiment, it is possible to not only remove the noise signal mixed into the biological information, but also detect the level of the noise included in the biological information. Thus, in the case where the noise level is too high, it is possible to take measures such as changing the measurement place of the biological information of the person-to-be-measured.

The embodiments of the sudden-onset signal processing device for biological information adapted to remove the effect of a sudden-onset signal have been described above; however, it is to be understood that the present invention is not limited to the embodiments described above, but includes various modifications and applications without departing from the scope of the claims of the present invention.

REFERENCE SIGNS LIST 10 adaptive delay device
11 variable delay device
12, 13 peak detector
14, 22 subtractor
15 comparator
16, 24 LPF (low-pass filter)
17 up/down counter
18 clock generator
19 ±comparator (comparator)
20 amplifier
23 absolute value circuit

The invention claimed is:

1. A sudden-onset signal processing device for detecting periodic biological information without being affected by a sudden-onset noise signal caused by a sudden-onset vibration, the device comprising:
 a variable delay device to which periodic biological information of a person-to-be-measured is inputted, a delay amount of the variable delay device being set equal to one cycle of a periodic biological information signal of the person-to-be-measured;
 a first peak detector that detects a peak value of an input signal of the variable delay device;
 a second peak detector that detects a peak value of an output signal of the variable delay device;
 a subtractor that performs subtraction between the output of the first peak detector and the output of the second peak detector;
 a first comparator that compares the output of the subtractor with a first threshold, and that outputs a positive output if the output of the subtractor is larger than the first threshold, and outputs a negative output if the output of the subtractor is smaller than the first threshold;
 a clock generator that generates a clock signal based on the output of the first peak detector;
 an up/down counter that is decremented if the output of the first comparator is a positive output, and is incremented if the output of the first comparator is a negative output, and that supplies an output to the variable delay device with a clock from the clock generator such that, even if a sudden-onset noise signal is mixed into the periodic biological information signal, no change in delay amount of the variable delay device will be caused, thereby avoiding influence of the sudden-onset noise signal on the detecting of the periodic biological information;
 a second comparator that compares the output of the subtractor with a second threshold having a positive threshold value and a negative threshold value, and generates an output signal if the absolute value of the output of the subtractor exceeds the absolute value of the second threshold; and
 an amplifier that is connected to the variable delay device, and whose gain is controlled by the output of the second comparator.

2. The sudden-onset signal processing device for biological information according to claim 1, wherein the output of the first comparator is supplied to the up/down counter through a low-pass filter.

3. The sudden-onset signal processing device for biological information according to claim 2, further comprising:
 a second subtractor that subtracts the biological information to be inputted to the variable delay device from an output signal of the amplifier;
 an absolute value circuit that obtains the absolute value of the output of the second subtractor; and
 a second low-pass filter that integrates the output of the absolute value circuit,
 wherein noise amount can be outputted as the output of the second low-pass filter.

4. A sudden-onset signal processing method for detecting periodic biological information without being affected by a sudden-onset noise signal caused by a sudden-onset vibration, the method comprising the steps of:
 detecting a peak of periodic biological information of a person-to-be-measured to be inputted to a variable delay device, a delay amount of the variable delay device being set equal to one cycle of a periodic biological information signal of the person-to-be-measured;
 detecting a peak of an output signal of the variable delay device;
 performing subtraction between a peak detection signal of the input of the variable delay device and a peak detection signal of the output of the variable delay device with a subtractor;
 comparing an output signal of the subtractor with a predetermined threshold with a comparator, and outputting a positive output if the output signal of the subtractor is larger than the threshold, and a negative output if the output signal of the subtractor is smaller than the threshold, from the comparator;
 decrementing an up/down counter if the output of the comparator is a positive output, and incrementing the up/down counter if the output of the comparator is a negative output;
 transferring the output of the up/down counter to the variable delay device with a clock generated based on the output of a peak signal of the biological information to be inputted to the variable delay device such that, even if a sudden-onset noise signal is mixed into the periodic biological information signal, no change in delay amount of the variable delay device will be caused, thereby avoiding influence of the sudden-onset noise signal on the detecting of the periodic biological information;
 generating a predetermined outputting voltage if the absolute value of the peak value of the output of the subtractor exceeds a predetermined second threshold; and
 supplying the outputting voltage to an amplifier connected to the output of the variable delay device, and controlling the amplifier so that the gain of the amplifier decreases only when the outputting voltage exists.

* * * * *